US005776098A

United States Patent [19]
Silver et al.

[11] Patent Number: 5,776,098
[45] Date of Patent: Jul. 7, 1998

[54] DIAPHRAGM PUMP AND PUMP MOUNTED IN A CARRYING CASE USEFUL IN BREAST PUMPING

[75] Inventors: Brian H. Silver, Cary; Larry D. Annis, Elgin, both of Ill.

[73] Assignee: Medela, Incorporated, McHenry, Ill.

[21] Appl. No.: 510,714

[22] Filed: Aug. 3, 1995

[51] Int. Cl.⁶ .................................................. A61M 1/06
[52] U.S. Cl. .................................................. 604/74
[58] Field of Search .................. 604/74, 73, 75, 604/76, 30, 31, 35–38, 118, 119, 120, 121

[56] References Cited

U.S. PATENT DOCUMENTS

| 1,596,520 | 8/1926 | Eskholme et al. | |
|---|---|---|---|
| 2,542,505 | 2/1951 | Gascoigne | 128/281 |
| 3,786,801 | 1/1974 | Sartorius | 128/2 F |
| 3,931,795 | 1/1976 | Duncan | 119/14.38 |
| 4,200,058 | 4/1980 | Happel | 119/14.01 |
| 4,249,481 | 2/1981 | Adams | 119/14.02 |
| 4,263,912 | 4/1981 | Adams | 128/281 |
| 4,323,067 | 4/1982 | Adams | 128/281 |
| 4,607,596 | 8/1986 | Whittlestone et al. | 119/14.02 |
| 4,673,388 | 6/1987 | Schlensog et al. | 604/74 |
| 4,740,196 | 4/1988 | Powell | 604/75 |
| 4,772,262 | 9/1988 | Grant et al. | 604/74 |
| 4,794,915 | 1/1989 | Larsson | 128/64 |
| 4,799,922 | 1/1989 | Beer et al. | 604/74 |
| 4,857,051 | 8/1989 | Larsson | 604/74 |
| 4,941,433 | 7/1990 | Hanauer | 119/14.02 |
| 4,964,368 | 10/1990 | Ball et al. | 119/14.49 |
| 4,964,851 | 10/1990 | Larsson | 604/74 |
| 5,007,378 | 4/1991 | Larson | 119/14.47 |
| 5,049,126 | 9/1991 | Larsson | 604/74 |
| 5,178,095 | 1/1993 | Mein | 119/14.47 |
| 5,218,924 | 6/1993 | Thompson et al. | 119/14.02 |
| 5,308,321 | 5/1994 | Castro | 604/74 |

FOREIGN PATENT DOCUMENTS

| 158 976 | 5/1957 | Denmark. |
| 33 28 725 | 2/1984 | Germany. |
| 2 082 920 | 3/1982 | United Kingdom. |
| 2 127 293 | 4/1984 | United Kingdom. |

OTHER PUBLICATIONS

"The Whittlestone Breastmilker" Model Havenwood Mk III Operating Manual.
"MEDAP" Milchsauger P 6010 . . . Betriebsanleitung Instruction Manual.

Primary Examiner—Michael Buiz
Assistant Examiner—Manuel Mendez
Attorney, Agent, or Firm—Brinks Hofer Gilson & Lione

[57] ABSTRACT

An motorized pump is disclosed that includes a flexible diaphragm fitting within a rigid member, a motor drive mechanism for drawing a puller member attached to the diaphragm away from the rigid member to create a space between the diaphragm and the rigid member and form a negative pressure region within that space, and an outlet communicating with the negative pressure region. In one embodiment, the pump provides a negative pressure source for a breastpump that is readily portable by virtue of the soft carrying case within which the diaphragm pump and motor are housed.

20 Claims, 5 Drawing Sheets 5,776,098

DIAPHRAGM PUMP AND PUMP MOUNTED IN A CARRYING CASE USEFUL IN BREAST PUMPING

BACKGROUND OF THE INVENTION

This invention relates to motorized pumps, and more particularly, to breastpumps.

Breastpumps are convenient for nursing mothers, because, among other things, they allow the nursing mother to draw off breast milk to feed to the child at a later time when the mother may not be present. For some mothers, breastpumps are required, particularly when the child has suckling difficulties, or if the mother has problems with excessive or deficient milk production, or cannot empty completely. Some mothers also require breastpumps in the event of soreness or injury of the mammilla, or sunken mammilla.

Manually-driven breastpumps are commonplace, primarily because they are inexpensive, relatively easy to manufacture, and readily transportable. However, they typically require the use of both hands to pump a single breast—one to hold the breast shield/pump in place, and the other to drive the pump. They also obviously require some manual effort to operate.

Motor-driven pumps for breastpumps, such as battery-powered or house-current powered, also have been marketed. While eliminating the need for manually operating the pump, those pumps made for operating two breast shield assemblies at once—double-pumping—have typically been quite large, and often quite heavy. Smaller battery-powered pumps which are part of the breast shield assembly itself have not historically been adapted to, or capable of, double-pumping off the same pump. Further, while carrying-cases for portable motor-drives for breastpumps have been developed, those cases are themselves typically specifically adapted for transportation of the motor-drive, generally comprising a rigid case from which the motor-drive is removed for use.

SUMMARY OF THE INVENTION

The present invention was designed with many of the foregoing considerations in mind. It has a principal objective to provide a relatively inexpensive but efficient pump that is readily portable because it is compact and lightweight. That portability has, in a preferred form of the invention, manifested itself in a pump which is mounted within a soft carrying case, and readily accessible for attachment to one or two breast shield assemblies through an opening provided in the side of the case.

The motor drive mechanism of the pump has a durable drive train, and the main vacuum-generating pump components—flexible diaphragm and rigid cap—are each detachably mounted together within a frame carried within the bag. Assembly, and disassembly—as for repair or cleaning—are therefore efficiently and easily accomplished. A pressure regulator valve mechanism formed on the rigid cap further provides simple manual control for varying negative pressure developed by the pump.

These features make the inventive pump ideally suited for a breastpump. The pump when housed within a soft carrying bag, is convenient for breastfeeding mothers to transport their breastpumps for use at other locations, such as the workplace.

More particularly, the present invention in one form is an electrically-powered diaphragm pump mounted within a support frame contained in a soft carrying case. A zippered flap in the carrying case provides access to the front of the pump unit, which has spigots for attaching tubing that connects to breast shield assemblies. In a preferred embodiment, the soft carrying case has a number of interior compartments for storage of items, such as breast shield assemblies and tubing.

The diaphragm pump in one form of the invention has a durable drive chain comprising a drive shaft fit with an eccentric cam, to which is attached a follower. The follower is in turn pivotably connected to a puller that is attached to a flexible diaphragm. The diaphragm rests near or against the interior surface of a rigid cap, the latter being stationarily mounted. In operation, the rotation of the drive shaft rotates the cam, causing the follower to move back and forth as it orbits the shaft on the cam. The puller moves with the follower, drawing the diaphragm away from the cap and forming a negative pressure that is communicated by one or two spigots to tubing attached to the breast shield assemblies.

The pump further can include a vacuum regulator device comprising a rotary valve member mounted for rotational movement on the rigid cap. An aperture is formed through the valve member. At least one hole is formed through the cap member, and communicates with the pressure region generated between the cap interior and the diaphragm.

The valve member has a first position wherein the valve aperture and the cap hole are aligned to place the pressure region in communication with atmosphere, and a covered position wherein the valve aperture and the cap hole are unaligned, with the valve member thereby closing the cap hole. A maximum and minimum vacuum level are thereby provided, depending on whether air can be drawn within the cap or not, as controlled by the valve.

A second hole different in size from the first cap hole can be additionally provided, establishing a second position wherein the valve aperture and the second cap hole are aligned for a different vacuum level. Maximum, medium and minimum vacuum levels can thus be made available through adjustment of the cap hole sizes.

Other features and advantages of the present invention will become apparent from the detailed description that follows taken in conjunction with the drawings, described below.

DETAILED DESCRIPTION OF A PREFERRED EMBODIMENT

A diaphragm pump of the present invention is shown in an embodiment as a vacuum (i.e., negative pressure) source for a breastpump. The diaphragm pump has uses in other environments and applications, however.

Figure 1:
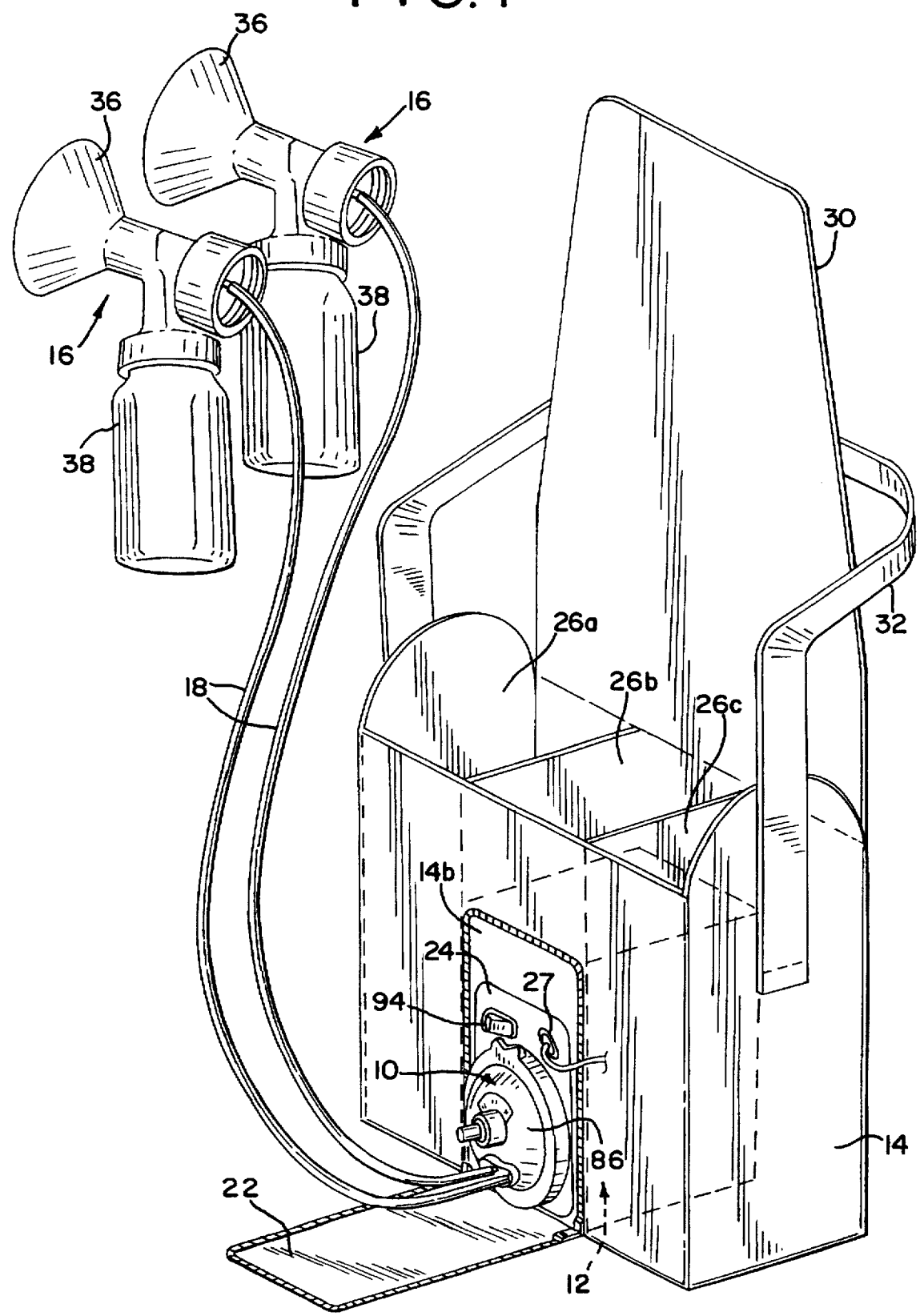
FIG. 1 is a perspective view of a diaphragm pump-driven breastpump in a soft carrying case made in accordance with the present invention.

Referring to FIG. 1, the diaphragm pump 10 is mounted within a rigid support frame 12. The support frame 12, which is somewhat boxlike, is carried and mounted within a soft carrying case or bag 14. It is shown connected to two breast shield assemblies 16 via tubing 18. Tubing 18 is attached at one end to respective spigots 20 (FIG. 2) via a slip-on fit over the spigots 20. With the tubing 18 removed from the spigots 20, the diaphragm pump 10 can be closed up within the case 14 via a zippered flap 22. Front plate 24 of the pump 10 may preferably be set back from the sidewall of the case 14 so that the zippered flap 22 is co-planar with the case front sidewall 14a when shut. A wall 21 is formed surrounding the spigots 20 to protect the spigots from being accidentally broken off.

Case 14 has a number of interior compartments 26a, 26b, 26c, which constitute storage areas, such as for the breast shield assemblies 16, tubing 18, diapers, etc. Case 14 also could include a power source in the form of a battery (not shown) to which a commonly obtainable 12 V DC gear motor 28 (FIG. 2) is electrically connected. An alternative power source could be an A.C. source (e.g., common 120 VAC service) through a DC converter, as at jack 27 (FIG. 1). The motor, power source and their various electrical connections are all conventional, and well known to those skilled in the art.

Case 14 has a flap-type closure 30, with a shoulder strap 32. Pump support frame 12 is fixed within a fabric compartment formed within the case 14. This may be by attachment of the front plate 24 to surrounding fabric 14b in a conventional manner, such as by riveting, stitching, adhering or some other common attachment. Here, front plate 24 frames the fabric 14b and captures it between the back of the plate 24 and the front 12a of the support frame 12. This is accomplished using toothed plastic rivets 34, or alternatively keyhole-type fasteners, which extend through the front plate 24, holes in the intervening fabric 14b, and then through holes provided in the front 12a of support frame 12.

The breast shield assemblies 16 are of the type sold by Medela, Inc. under the name MANUALECTRIC, and generally shown in U.S. Pat. Nos. 4,857,051 and 4,929,229, for example. The assemblies 16 have a breast shield 36 associated with a milk bottle 38. A periodic vacuum generated by the pump 10 within the shield 16 serves to extract milk, which is then collected in the bottle 38.

Pump 10 has a guide 40 (FIG. 3) fixedly mounted to an inner frame wall 12b, as by machine screws (see hole 41 provided to this end). An opening 42 is made in the guide 40 through which drive shaft 44 of the motor 28 extends. The diameter of the opening 42 is wider than the drive shaft 44 so that the latter freely rotates. Guide 40 has an elongated slot 45 formed therein which serves to confine and direct the movement of a guide pin 46 extending from a puller 48 connected to a follower 50 in a manner to be described hereafter.

Figure 6:
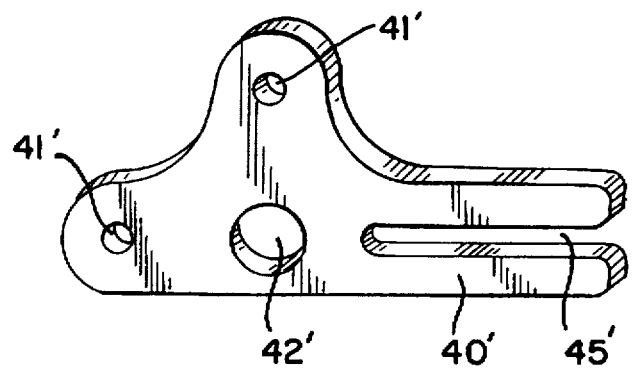
FIG. 6 is a perspective view of an alternative embodiment of a guide for the diaphragm pump.

FIG. 6 illustrates an alternative embodiment for the guide. Guide 40' functions in the same manner as guide 40. It is mounted to the inner frame wall 12b using machine screws through holes 41', and has an elongated slot 45' for the guide pin 46. Drive shaft 44 extends through hole 42'.

A cam 52 is mounted on the drive shaft 44. A collar-like portion 53 is formed off-center on the cam. The outboard end of the drive shaft 44 is received in a D-shaped opening 54 within the collar portion 53, with the drive shaft 44 keyed to the same shape in a snug fit.

An aperture 56 is also formed off-center in the cam 52. When cam 52 is driven by the motor 28, aperture 56 orbits around the drive shaft 48.

Figure 2:
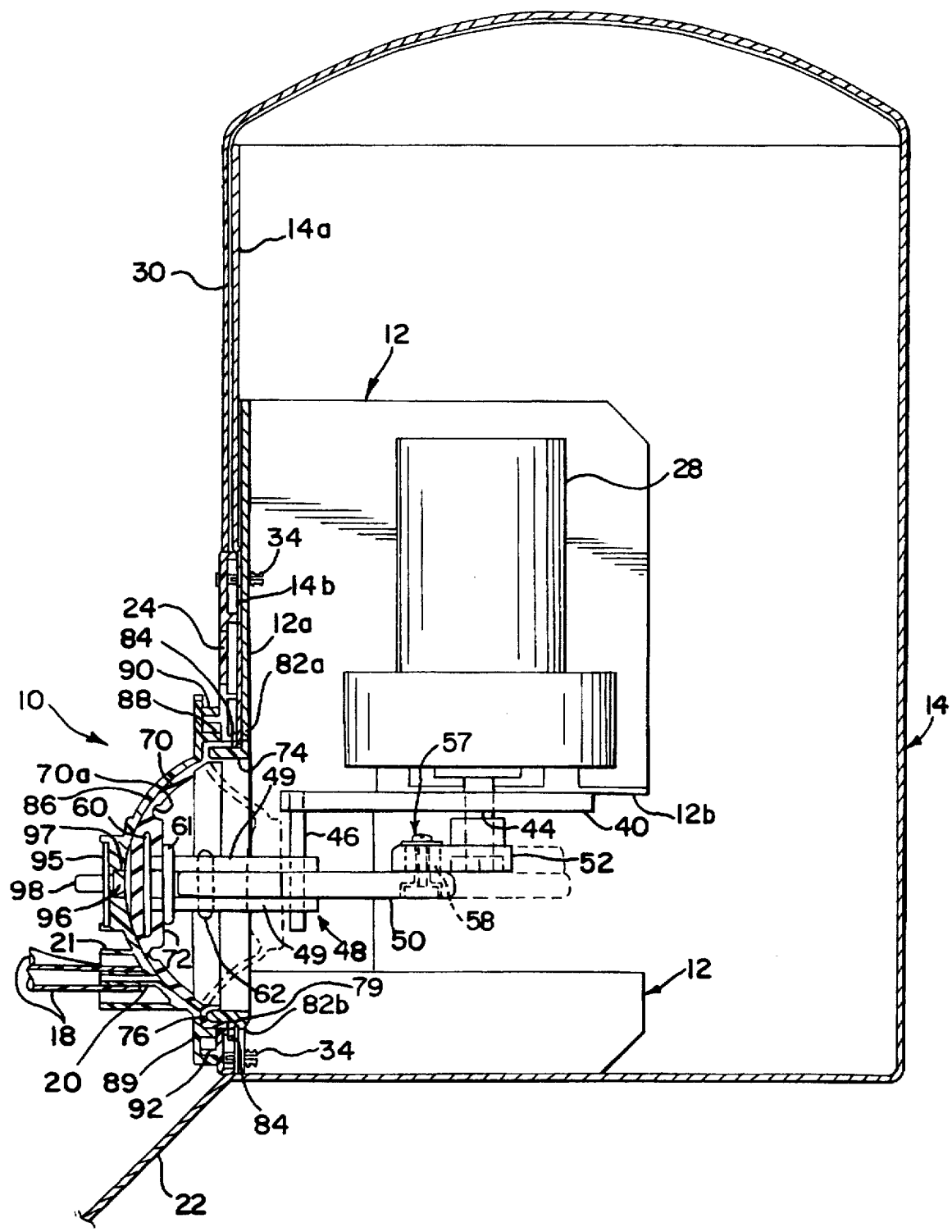
FIG. 2 is a cross-sectional view of the breastpump of FIG. 1 showing the diaphragm pump housed within the closed soft carrying case.
Figure 3:
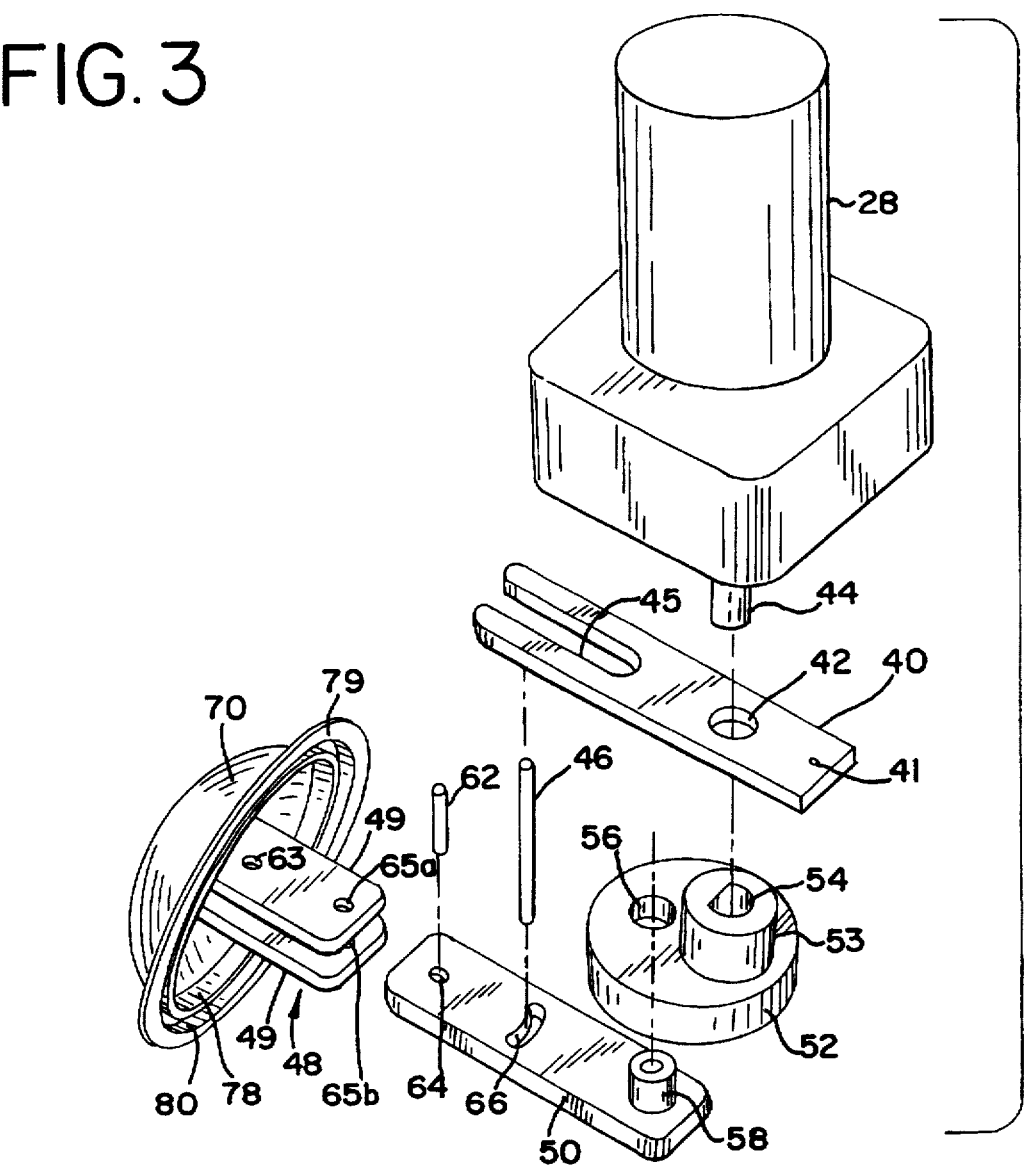
FIG. 3 is an exploded perspective view of most of the elements of the diaphragm pump.
Figure 5:
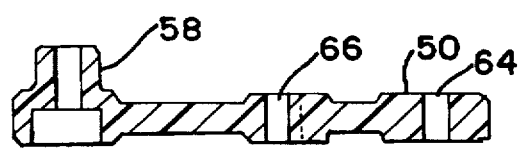
FIG. 5 is a cross-sectional view along line 5—5 of FIG. 4.
Figure 4:
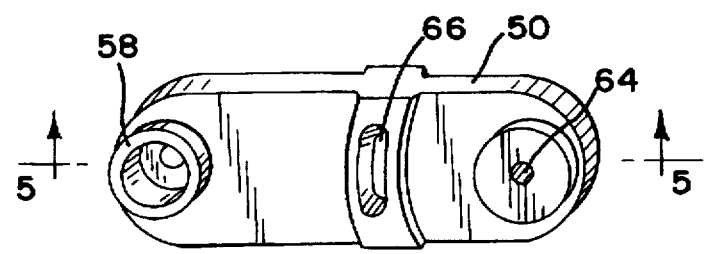
FIG. 4 is a top view of a follower.

Follower 50 (FIG. 3) is operably connected to the cam 52 via a hollow post 58 formed adjacent the rearward end of the follower 50. Post 58 has a diameter which is slightly smaller than that of the aperture 56 of the cam 52 within which it is received to freely rotate. For purposes of relative scale, the follower 50 shown herein has a longitudinal length of about 2.5 inches, and a lateral width of about 0.75 inch. A machine screw, washer and lock-nut combination 57 is additionally used for further, but movable fixation (FIG. 2). An alternative embodiment of follower 50 is shown in FIGS. 4 and 5.

On the forward end of the follower 50 is mounted the puller 48. Puller 48 has two parallel legs 49 which extend from a puller cap 59 formed of an end disk 60 and a disk-like flange 61 spaced slightly inboard from the end disk 60. Puller 48 is connected to the follower 50 via a spring pivot pin 62 which extends through and is fixed within holes 63 in the legs 49 (only one of which holes 63 is shown in FIG. 3), and extends through hole 64 in the follower 50. The follower 50 is thus captured between the legs 49, but can pivot on the pivot pin 62. A guide pin 46, which is fixed within holes 65a, 65b in the legs 49, extends through a crescent-shaped aperture 66 formed in follower 50. When the follower 50 is mounted to the cam 52, guide pin 46 extends into the slot 45 of the guide 40 (FIG. 2).

A flexible diaphragm 70 is mounted on the end of the puller 48. Diaphragm 70 is preferably made of silicone rated for food contact, and has a general semi-spherical shape. End disk 60 of the puller 48 is received within an orifice in the inboard side of the diaphragm 70 which orifice is formed by a thickened center part of the diaphragm 70 and a circular overlying flange part 72 (see FIG. 9). End disk 60 fits within this orifice in a button-like engagement. Flange disk 61 on the puller 48 presses against the flange part 72 of the diaphragm to further enhance the engagement. It will be noted that a circumferential reduced wall thickness is formed in the diaphragm at 70a around the center area of the diaphragm 70 to facilitate flexion of the diaphragm. The wall thickness of the portion of the diaphragm 70 between the thickened center part and approximately the perimeter of the curved portion of the diaphragm is generally about 0.08 in.

Figure 9:
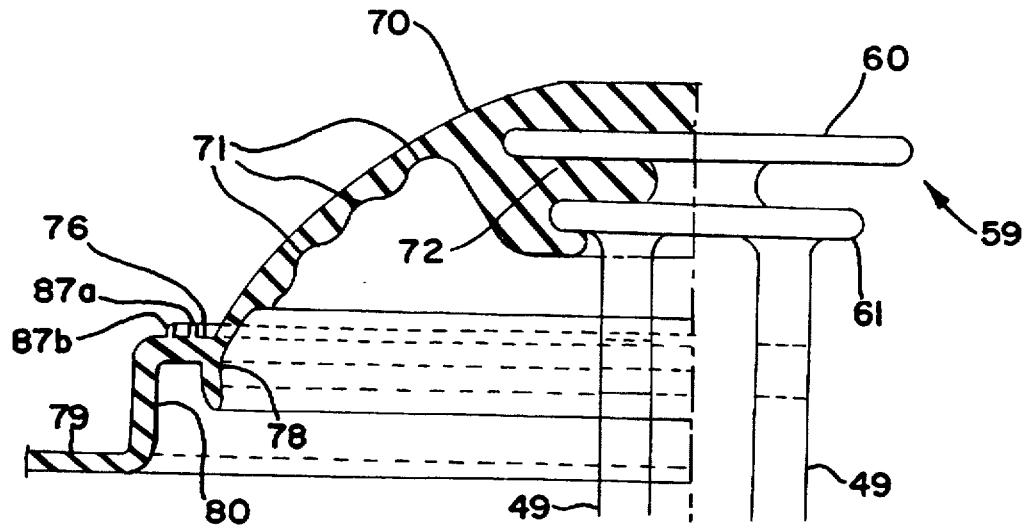
FIG. 9 is an enlarged partial view in section of an alternative form of the diaphragm.

An alternative form for the diaphragm wall is shown in FIG. 9. As shown in that figure, a corrugated or rippled interior provided by concentric channels 71 facilitate flexion of the diaphragm 70.

Figure 8:
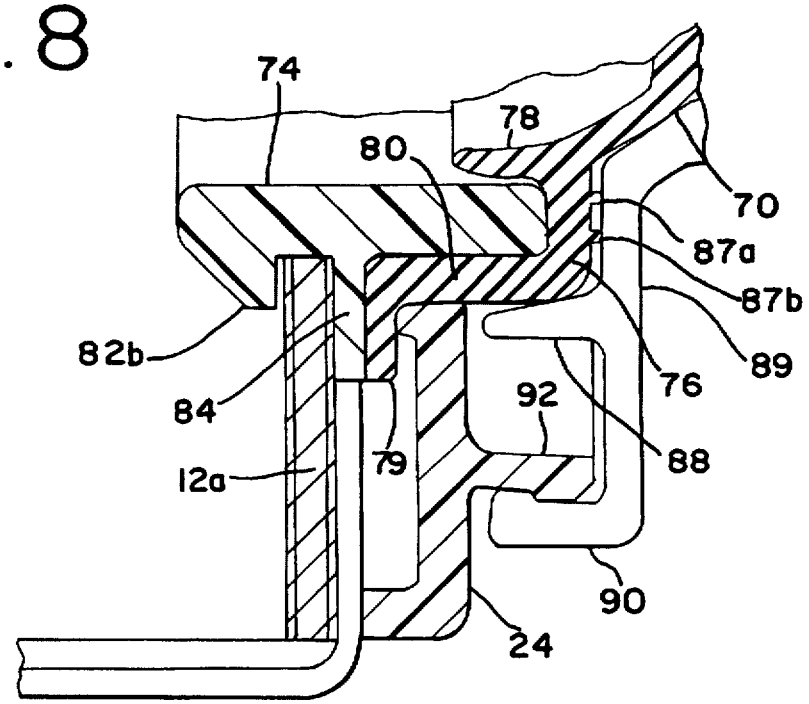
FIG. 8 is an enlarged partial view in section of the diaphragm pump mounting arrangement shown in FIG. 2.

As shown in FIGS. 2 and 8, diaphragm 70 is mounted to the front plate 24 using a diaphragm mounting ring 74. Diaphragm 70 has a perimetrical shoulder 76 formed thereon from which depend inner and outer concentric circular flanges 78 and 80, respectively. With shoulder 76, flanges 78 and 80 form a circular channel. The outboard part of mounting ring 74 is received within this channel in a slip-on type fit of the diaphragm.

With the diaphragm 70 so mounted thereon, mounting ring 74 is received in an aperture formed in the front plate 24 and the frame front 12a. Two locking tabs 82a, 82b extend outwardly at opposite sides of the mounting ring, and engage within cut-outs formed in the aperture of the frame front 12a to position the mounting ring.

A thin-width ring 84 is formed around the outside circumference of the mounting ring 74. This ring 84 underlies an outwardly extending lip 79 provided on the diaphragm 70, which lip 79 is pressed between the front plate 24 and the ring 84.

Figure 7:
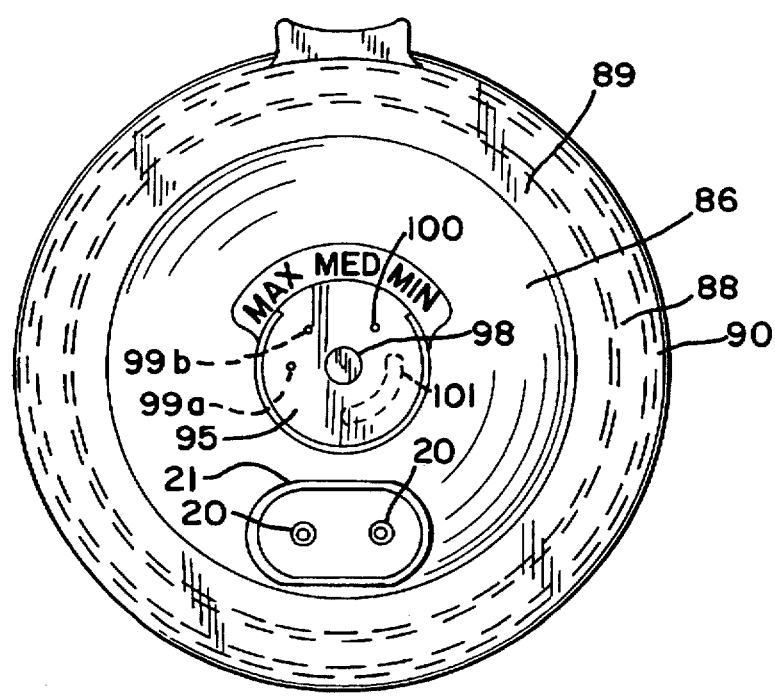
FIG. 7 is a front view of the diaphragm pump cap.

Overlying the diaphragm 70 is a rigid housing cap 86 made of polypropylene. Cap 86 has an inner surface roughly matching the curvature of the diaphragm 70, such that the diaphragm rests close to or against the interior surface of the cap 86. The cap 86 has a ring-like portion 89 extending outwardly from the edge of the semi-spherical dome portion of the cap 86. Concentric inner and outer cap flanges 88 and 90, respectively, depend from the ring-like portion 89 (see FIGS. 7 and 8 in particular). Inner cap flange 88 presses against the outboard side of outer diaphragm flange 80, with part of ring-like portion 89 overlying diaphragm shoulder 76. In conjunction with the mounting ring 74, this forms an air seal between the cap 86 and the underlying diaphragm 70. Additional concentric ribs 87a, 87b are formed on top of the diaphragm shoulder 76 out of the same material as the diaphragm, and serve to facilitate this seal through compression against the cap shoulder 89. Outer flange 90 of the cap 86 is received in a snap-engagement with a cap mounting ring 92 formed on the face of the front plate 24 to mount the cap 86 in place.

In operation of the pump 10, motor 28 is actuated, as by a standard on-off circuit utilizing switch 94 mounted in the front plate 24. Drive shaft 44 rotates cam 52 causing follower 50 to move rearwardly (relative to the front plate 24) and then forwardly. Puller 48 in turn moves rearwardly with the follower 50, drawing diaphragm 70 away from the inside of the cap 86. This generates a negative pressure (vacuum) in the space thus formed between diaphragm 70 and cap 86 (see dotted-line position of the drive chain elements and diaphragm in FIG. 2).

The rotation of the cam 52 with its movement of the pivotable follower 50 is designed to generally generate and follow the type of vacuum curve, and cycles per minute, shown and described in Medela U.S. Pat. No. 5,007,899. Guide 40 serves to constrain the pivoting movement between the puller 48 and follower 50.

Figure 10:
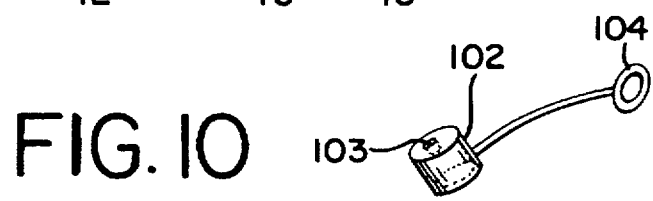
FIG. 10 is a perspective view of a cap for use with the pump spigots.

That negative pressure generated within the cap 86 is communicated through the outlet provided by the spigots 20 to one or both of the tubes 18 (depending on whether one or two breast shield assemblies 16 are being used). If only one breast shield assembly 16 is being used, it is contemplated that a cap 102 (FIG. 10) would be used to close the spigot 20 not being used. The cap 102 would further include a small pinhole vent 103 designed to nonetheless admit some air through the spigot and thereby into the cap interior in a manner to normalize the vacuum between single and double pumping usage, i.e., so that the vacuum drawn in a shield is about the same when only using one breast shield as when both breast shield assemblies are attached. Cap 102 has a loop end 104 to tether the cap 102 to one of the spigots 20.

A vacuum regulator is additionally provided for adjustment of the level of vacuum from the pump. This regulator takes the form of a flap-type valve disk 95 (FIG. 7) mounted in a circular-shaped depression formed in the center of cap 86. Valve disk 95 has a knob 96 (FIG. 2) which is received in a lipped aperture 97 formed in the foregoing depression, in a pop-in fit. A knurled stem 98 extends from the valve disk 95 which is grasped to rotate the valve.

When valve disk 95 is rotated, a hole 100 through the disk 95 can be aligned with one or the other of holes 99a, 99b (FIG. 7) extending through the depression into the interior of the cap dome, or placed out of alignment with either hole 99a, 99b, the latter both then being covered and closed by the valve disk 95. Holes 99a and 99b are of different diameters, such that more air will pass through one than the other when aligned with disk hole 100. Accordingly, a preset "medium" (smaller diameter hole), "minimum" (larger diameter hole) or "maximum" (both holes covered) vacuum level range is provided. Crescent-shaped aperture 101 formed through the cap 86, which is under the disk valve 95, serves to vent air admitted into the cap interior (within the diaphragm/cap space created by the vacuum stroke) on the forward or compression stroke of the diaphragm 70 (diaphragm 70 moving toward the cap interior).

A diaphragm pump is thus provided which is of relatively small size, with a durable drive chain. In the disclosed environment of a breastpump, it fits handily within a soft carrying case for quick and easy hook-up to one or more breast shield assemblies, which can be carried in the case.

It is envisioned that a thin disposable membrane-like cover (not shown) may additionally be provided over the diaphragm 70. This disposable cover would be between the diaphragm 70 and inside of the cap 86, and serve to further hygienically isolate the diaphragm 70 from any milk, air or the like which could be pulled within the cap 86 in the vacuum stroke. This disposable cover would be particularly useful if there were multiple users of the pump 10. Cap 86 would simply be removed and sterilized, and the disposable cover replaced between users. Alternatively, a separate cap 86, which itself might be disposable, for each user with a disposable cover could be provided.

What is claimed is:

1. A pump comprising:
    a flexible diaphragm,
    a first mounting ring upon which said flexible diaphragm is releasably attached,
    a rigid member,
    a second mounting ring upon which said rigid member is releasably attached,
    an air seal formed between said diaphragm and said rigid member,
    a puller member attached to said flexible diaphragm,
    a drive member connected to said puller member which drive member is adapted to draw said puller member along with said diaphragm away from said rigid member, thereby creating a space between said diaphragm and said rigid member and forming a pressure region within said space,
    a motor drive mechanism including said drive member to reciprocate said puller member to first draw said puller member away from said rigid member and then move said puller member back toward said rigid member, and
    an outlet in communication with said space between said diaphragm and said rigid member.

2. The pump of claim 1 further including a base, said first mounting ring being releasably fixed to said base.

3. The pump of claim 2 wherein said base has an aperture within which said first mounting ring is releasably received and held in place.

4. The pump of claim 3 wherein said base has said second mounting ring formed thereon.

5. The pump of claim 1 wherein said rigid member has a circumferential flange which engages said diaphragm and presses said diaphragm against said first mounting ring to form said air seal.

6. The pump of claim 1 wherein said diaphragm has a circumferential channel formed thereon which is received in a slip-on fit on said first mounting ring, and said rigid member has a circumferential flange which engages said diaphragm and presses said diaphragm against said first mounting ring to form said air seal.

7. The pump of claim 1 wherein said rigid member has a semi-spherical concavity and said diaphragm has a complementary semi-spherical shape to that of said rigid member, with said diaphragm nesting within said rigid member concavity in a first position.

8. A pump for use in expressing mother's milk, said pump being adapted for generating a periodic pressure in two breast shield assemblies in use at the same time, comprising:
   a flexible diaphragm,
   a rigid member,
   an air seal formed between said diaphragm and said rigid member,
   a puller member attached to said flexible diaphragm,
   a drive member connected to said puller member which drive member is adapted to draw said puller member along with said diaphragm away from said rigid member, thereby creating a space between said diaphragm and said rigid member and forming a single pressure region within said space,
   a motor drive mechanism including said drive member to reciprocate said puller member to first draw said puller member away from said rigid member and then move said puller member back toward said rigid member, and
   a pair of outlets in communication with said space between said diaphragm and said rigid member, each of said outlets being connectable to a respective breast shield assembly.

9. The pump of claim 8 further including a closure member for closing one of said outlets when said pump is used with a single breast shield assembly, said closure member including a relief port for allowing a predetermined amount of air to flow into said pressure region when a negative pressure is generated within said pressure region.

10. A breastpump for use in the extraction of mother's milk comprising:
   a pump for generating a periodic pressure which pressure is conveyable through an outlet on said pump to a breast shield assembly used in the extraction of mother's milk, and
   a soft carrying case within which said motor and pump are mounted, said soft carrying case having a wall with said outlet mounted therein such that said pump outlet is accessed from the exterior of said carrying case, but substantially concealed from view by a portion of said carrying case when said breast pump is not in use.

11. The breastpump of claim 10 wherein said soft carrying case further comprises at least one storage compartment formed inside said case.

12. A breastpump for use in the expression of mother's milk comprising:
   a motor drive mechanism,
   a pump for generating a periodic pressure which pressure is conveyable through an outlet on said pump to a breast shield assembly used in the extraction of mother's milk, said pump including
   a flexible diaphragm,
   a rigid member,
   an air seal formed between said diaphragm and said rigid member,
   a puller member attached to said flexible diaphragm,
   a drive member connected to said puller member which drive member is adapted to draw said puller member along with said diaphragm away from said rigid member, thereby creating a space between said diaphragm and said rigid member and forming a pressure region within said space,
   said motor drive mechanism including said drive member to reciprocate said puller member to first draw said puller member away from said rigid member and then move said puller member back toward said rigid member,
   said outlet being in communication with said space between said diaphragm and said rigid member,
   and a soft carrying case within which said motor and pump are mounted, said soft carrying case having an opening through which said pump outlet is accessed.

13. The breastpump of claim 12 further including a support frame to which said motor and pump are fixed, said support frame being stationarily mounted within said carrying case, a first mounting ring upon which said flexible diaphragm is releasably attached being releasably fixed to said frame.

14. The breastpump of claim 13 wherein said support frame has an aperture within which said first mounting ring is releasably received and held in place, said support frame further having a second mounting ring thereon upon which said rigid member is releasably attached.

15. The breastpump of claim 13 wherein said rigid member has a circumferential flange which engages said diaphragm and presses said diaphragm against said first mounting ring to form said air seal.

16. The breastpump of claim 13 wherein said diaphragm has a circumferential channel formed thereon which is received in a slip-on fit on said first mounting ring, and said rigid member has a circumferential flange which engages said diaphragm and presses said diaphragm against said first mounting ring to form said air seal.

17. A breastpump comprising:
   a pump for generating a periodic vacuum pressure which pressure is conveyed to an outlet of said pump to which a breast shield assembly used in the extraction of mother's milk is connectable;
   a motor to drive said pump;
   a soft-sided carrying case within which said motor and pump are mounted, said carrying case having sidewalls, a bottom wall and a top, with said outlet of said pump being mounted in a sidewall and accessible from the exterior of said carrying case.

18. The breastpump of claim 17 wherein said breast shield assembly includes a breast shield adapted to be placed over a breast and tubing connecting with the interior of said breast shield for conveying air pressure changes, said outlet comprising a pair of ports, each of said ports being adapted to be connected to said tubing, and a cover attached to said carrying case and overlying said ports, said cover being movable away from said outlet to expose said ports.

19. The breastpump of claim 17 wherein said breast shield assembly includes a breast shield adapted to be placed over a breast and tubing connecting with the interior of said breast shield for conveying air pressure changes, said outlet comprising at least one port, said port being adapted to be connected to said tubing, and a cover attached to said carrying case and overlying said ports, said cover being movable away from said outlet to expose said ports.

20. The breastpump of claim 17 wherein said motor and said pump are mounted in a rigid frame fixed within the interior of said carrying case, said outlet being located on a base mounted in a sidewall of said carrying case, said base further including a switch connected with circuitry for actuating said pump, and a vacuum regulating device mounted on said base and in communication with said pump for adjusting said pressure, with a flap connected to said carrying case and overlying said base, said flap being releasably attached to said carrying case at one end to cover and uncover said base, said carrying case further having a storage area formed therein for carrying articles, and a shoulder strap attached to said carrying case.

* * * * *

UNITED STATES PATENT AND TRADEMARK OFFICE
CERTIFICATE OF CORRECTION

PATENT NO. : 5,776,098
DATED : July 7, 1998
INVENTOR(S) : Silver et al.

It is certified that error appears in the above-identified patent and that said Letters Patent is hereby corrected as shown below:

Column 7,
Line 44, insert -- a motor, -- after "milk comprising:"
Line 52, change "but substantially concealed from view by portion of said carrying case when said breast pump is not in use." to -- , said motor, pump and outlet being substantially concealable from view by a portion of said carrying case. --

Column 8,
Line 54, delete ".", insert -- , but substantially concealed from view by a portion of said carrying case when said breast pump is not in use. -- after "from the exterior of said carrying case."

Signed and Sealed this

Twenty-ninth Day of June, 2004

JON W. DUDAS
*Acting Director of the United States Patent and Trademark Office*